(12) United States Patent
Schwartz-Albiez et al.

(10) Patent No.: US 9,365,824 B2
(45) Date of Patent: Jun. 14, 2016

(54) METHOD FOR EXPANDING POSTEMBRYONIC STEM AND PROGENITOR CELLS FROM UMBILICAL CORD BLOOD AND IMMUNOTHERAPEUTIC AGENT

(75) Inventors: Reinhard Schwartz-Albiez, Galberg (DE); Michael Punzel, Weeze (DE)

(73) Assignee: IPD-THERAPEUTICS B.V., Bilthoven (NL)

( * ) Notice: Subject to any disclaimer, the term of this patent is extended or adjusted under 35 U.S.C. 154(b) by 2106 days.

(21) Appl. No.: 10/594,382

(22) PCT Filed: Mar. 31, 2005

(86) PCT No.: PCT/EP2005/003403
§ 371 (c)(1),
(2), (4) Date: Sep. 11, 2008

(87) PCT Pub. No.: WO2005/095584
PCT Pub. Date: Oct. 13, 2005

(65) Prior Publication Data
US 2009/0004150 A1    Jan. 1, 2009

(30) Foreign Application Priority Data
Mar. 31, 2004   (WO) ................. PCT/EP2004/003429

(51) Int. Cl.
C12N 5/00       (2006.01)
C12N 5/0789     (2010.01)

(52) U.S. Cl.
CPC .......... *C12N 5/0647* (2013.01); *C12N 2501/90* (2013.01); *C12N 2501/91* (2013.01)

(58) Field of Classification Search
None
See application file for complete search history.

(56) References Cited

FOREIGN PATENT DOCUMENTS

DE         102 45 927 A     4/2004

OTHER PUBLICATIONS

Theunissen, et al., "Long-term engrafting umbilical cord blood cells are preserved after ex vivo culture in stroma-free culture," *Online*! May 2001, http://mmserver.cjp.com/ gems/blood/ABMT.10.verfaillie.pdf, pp. 599-603.

Pankaj, et al., "Human LTC-IC can be maintained for at least 5 weeks in vitro when interleukin-3 and a single chemokine are combined with o-sulfated heparin sulfates: Requirement for optimal binding interactions of heparin sulfate with early-acting cytokines and matrix proteins," *Blood* Jan. 2000, 95(1):147-155.

Pankaj, et al., "Structurally specific heparin sulfates support primitive human hematopoiesis by formation of a multimolecular stem cell niche," *Blood* Dec. 1998, 92(12):4641-4651.

Lewis, et al., "Umbilical cord blood cells capable of engrafting in primary, secondary, and tertiary xenogeneic hosts are preserved after ex vivo culture in a noncontact system," *Blood* Jun. 2001, 97(11):3441-3449.

Schubert, "Einfluss regioselektiv modifizierter Heparansulfate auf den Erhalt and die Expansion primitiver hamatopoietischer Stammzelle and Vorlauferzellen," *Online*! 2004, http://doctor-schubert.de/downloads/Dissertation%20M.Schubert.pdf.

Punzel, et al., "The microenvironment of AFT024 cells maintains primitive human hematopoiesis by counteracting contact mediated inhibition of proliferation." *Cell Communication & Adhesion*, May-Jun. 2002, 9(3):149-159.

Gupta, et al., "Artificial 'proteoglycan-like' molecules containing heparin sulfate enhance the ability of cytokines to maintain human hematopoietic stem cells in vitro," *Journal of Investigative Medicine*, 1995, 43(SUPPL2):342A.

Moore et al., "In vitro maintenance of highly purified, transplantable hematopoietic stem cells," *Blood*, 1997, 89(12):4337-4347.

Moore, et al., "Hematopoietic Activity of a Stromal Cell Transmembrane Protein Containing Epidermal Growth Factor-Like Repeat Motifs," *Proceedings of the National Academy of Sciences of USA*, Apr. 1997, 94:4011-4016.

Stringer, et al., "Identification of an MIP-1alpha-binding heparin sulfate oligosaccharide that supports long-term in vitro maintenance of human LTC-ICs," *Blood*, Mar. 2003, 101(6):2243-2245.

*Primary Examiner* — Blaine Lankford
(74) *Attorney, Agent, or Firm* — Hoffmann & Baron, LLP

(57) ABSTRACT

Method for obtaining and expanding postembryonic hematopoietic stem cells from umbilical cord blood while avoiding unwanted differentiation. Initial cells from umbilical cord blood are proliferated and multiplied ex vivo in a stroma-free medium and in the presence of a regio-modified glycan or glycosaminoglycan. The regio-modified glycan or glycosaminoglycan, e.g. a heparin derivative, is N-desulfated, and N-reacetylated or N-reacylated, in essence, on C2 atoms. The heparin derivative advantageously comprises less than 5 percent of C3-O-sulfate, at least 60 percent C2-O-sulfate, and it is preferably added in a quantity of 15 to 50 mg/L to the medium in order to stop an unwanted differentiation. The stem cells generated in this manner can differentiate, after expansion, into myeloma cells and lymphatic cells, and they can be used as an immunotherapeutic agent against many diseases.

12 Claims, No Drawings

METHOD FOR EXPANDING POSTEMBRYONIC STEM AND PROGENITOR CELLS FROM UMBILICAL CORD BLOOD AND IMMUNOTHERAPEUTIC AGENT

This application is the U.S. National Phase of, and Applicant claims priority from, International Application Number PCT/EP04/003429 filed 31 Mar. 2004 which is incorporated herein by reference.

FIELD OF THE INVENTION

The present invention relates to methods for the ex vivo expansion of human postembryonic stem and progenitor cells from umbilical cord blood. In particular, the invention relates to the extraction, propagation and differentiation of human postembryonic stem and progenitor cells into immunocompetent cells for the purpose of using them as immunotherapeutic agents.

BACKGROUND OF THE INVENTION

Methods for the extraction and cultivation of stem cells have long been investigated; see Punzel M et al, The microenvironment of AFT024 cells maintains primitive human hematopoiesis by counteracting contact mediated inhibition of proliferation, CELL COMMUNICATION & ADHESION (2002), 9, 149-159; Gupta P et al. Human LTC-IC can be maintained for at least 5 weeks in vitro when interleukin-3 and a single chemokine are combined with O-sulfated heparansulfates Requirement for optimal binding interactions of heparinsulfate with early-acting cytokines and matrix proteins, BLOOD (2000) 95, 147-155; Gupta P et. al., Artificial proteoglycan-like molecules containing heparin sulfate enhance the ability of cytokines to maintain human hematopoietic stem cells in vitro, JOURNAL OF INVESTIGATIVE MEDICINE (1995) 43, 342A, & CLINICAL RESEARCH MEETING; SAN DIEGO; Calif.; USA; May 5-8, 1995; Gupta P et. al., Structurally specific heparin sulfates support primitive human hematopoiesis by formation of a multimolecular stem cell niche, BLOOD (1998) 92, 4641-4651; Lewis I D et al, Umbilical cord blood cells capable of engrafting in primary secondary, and tertiary xenogeneic hosts are preserved after ex vivo culture in a noncontact system BLOOD (2001) 97, 3441-3449; Moore K et al., In vitro maintenance of highly purified transplantable hematopoietic stem cells, BLOOD (1991) 89, 4337-4347; Moore K et. al., Hematopoietic activity of a stromal cell transmembrane protein containing epidermal growth factor like repeat motifs, PNAS USA (1997), 94, 4011-4016; Stringer S E et al., Identification of an MIP-1alpha-binding heparin sulfate oligosaccharide that supports long-term in vitro maintenance of human LTC-ICs. BLOOD (2003) 101, 2243-2245).

In Blood (2001) 97, 3441-3449, Lewis I D et al. describe ex vivo cultures with and without contact with stroma cells for the purpose of long-term maintenance and cultivation (expansion) of supposedly pluripotent cells from umbilical cord blood. The stem cells from umbilical cord blood are cultivated in collagen-coated culture dishes, where the stem cells are in fluid contact with AFT024 feeder cells through a membrane. Obviously, the AFT024 feeder cells release an unknown factor effecting the differentiation arrest during the expansion of the stem cells. Moreover, they describe expansion cultures in a uniform stroma-free MV8 medium containing additional N-desulfated O-sulfated heparin. The culture in the stroma-free MV8 medium with the N-desulfated O-sulfated heparin allows a 180-fold expansion of the TNC cells with the propagation of the $CD34^+$ cells or the CFC and LTC-IC expansions, however, being only one- to twofold. In this context, it is remarkable that the expansion of the $CD34^+$ cells in the stroma-free MV8 medium after seven days is only 1.1-fold (±0,2), and only 2.0-fold after 14 days, with a variance of ±2.0 (!!) (see table 2, page 3444), so that an expansion of the $CD34^+$ cells may not be assumed. In addition, stem cells multiplied in this manner only have limited capability for autoregeneration and multilinear differentiation into myeloid and erythroid cells according to an LTC-IC assay. Stem cells multiplied in this manner cannot differentiate into lymphatic cells (NK and NKT cells).

The prior art therefore has the disadvantage that the expansion of the stem and progenitor cells is very small and that no therapeutically applicable therapeutic agents can be manufactured due to the small number of cells. Moreover, the stem and progenitor cells are not multiplied such that they are still able to differentiate into Immunocompetent lymphatic cells afterwards.

SUMMARY OF THE INVENTION

It is the object of the invention to provide methods and means for expanding postembryonic stem and progenitor cells, preferably from umbilical cord blood, which is characterized in that, after ex vivo cultivation and successful propagation, the cells can differentiate into immunocompetent lymphatic NK and NKT cells as well as myeloid progenitors. For the intended use of the stem and progenitor cells as a therapeutic agent it is necessary that the ex vivo cultivation and expansion take place without the presence of stroma and feeder cells.

This object is solved by the postembryonic stem and progenitor cells being expanded in a medium which, apart from the usual nutrients, contains a specifically regio-modified glycan and/or glycosaminoglycan wherein, in particular, the $C_2$ atom in one or more monomer units is acylated or acetylated, and wherein the $C_6$ atom is O-sulfated. Thus, one aspect of the invention is a method for the extraction and expansion of postembryonic haematopoietic stem cells from umbilical cord blood while avoiding unwanted differentiation, wherein initial cells from umbilical cord blood are cultivated ex vivo in a stroma-free medium in the presence of a regio-modified glycan and/or glycosaminoglycan that is modified In such a manner that the side group of the $C_2$ atom of one or more monomer units of the glycan and/or glycosaminoglycan has an acetyl or acyl group with 2 to 12 carbon atoms; that the side group of the C6 atom of one or more monomer units of the glycan and/or glycosaminoglycan is a 6-O-sulfate group, and finally, the extraction of stem cells and progenitor cells that can differentiate into myeloid and lymphatic cells. The regio-modified glycan or glycosaminoglycan is preferably selected from α1-4 glycans, β1-3 glycans, β1-4 glycans, β1-3, β1-4 glycosaminoglycans, β1-4, α1-4 glycosaminoglycans, β1-4, β1-3, (α1-3) glycosaminoglycans und β1-4, β1-3, (α1-4) glycosaminoglycans. The regio-modified glycosaminoglycan can be a heparin derivative, which has essentially been N-desulfated and N-reacetylated or N-reacylated at the C2 atom, which has C6-O-sulfate groups, and which comprises 5 percent pr less C3-O-sulfate. Particularly preferably, the heparin derivative thus regio-modified comprises at least 60% C2-O-Sulfate and at least 80% C6-O-Sulfate. According to the invention, the regio-modified glycan or glycosaminoglycan is present in the culture medium in a concentration of 15 to 50 mg/L.

It is a further aspect of the invention that the stem cell properties of the stem and progenitor cells generated in this manner are controlled in an ML-IC assay, or, with regard to their lymphatic or myeloid properties, in an LY-IC assay and an LTC-IC assay. The stem and progenitor cells multiplied under conditions conforming to GMP (GMP—good manufacturing practice) can also be differentiated into functional lymphocytes (NK cells and NKT cells).

A particularly valuable aspect of the invention relates to a therapeutic composition comprising stem and progenitor cells extracted and multiplied according to the invention, preferably together with a pharmaceutically acceptable carrier, excipient or either diluting agent, for example for an intraperitoneal, intervenous, intrarectal or other injection.

Furthermore, an immediate aspect of the invention is a culture medium for expanding postembryonic stem and progenitor cells comprising a regio-modified glycan and/or glycosaminoglycan, wherein the side group of the C2 atom of one or more monomer units of the glycan and/or glycosaminoglycan is acylated or acetylated, and wherein the side group of the C6 atom of one or more monomer units of the glycan and/or glycosaminoglycan is a 6-O-sulfate group, as well as the use of such regio-modified glycans and glycosaminoglycans for expanding postembryonic stem and progenitor cells.

The therapeutic agent manufactured according to the invention can be administered directly and for the treatment of tumorous diseases, viral diseases, hepatitis C, HIV, malignant system diseases, acute leukaemias, chronic leukaemias, myeloproliferative syndrome (MPS), myelodysplastic syndrome (MDS), high-grade malignant non-Hodgkin lymphomas (NHL), low-grade malignant NHLs. Hodgkin's disease, multiple myeloma, Waldenström's syndrome, histiocytosis X, amyloidosis and solid tumors such as anal carcinoma, astrocystoma, basalioma, pancreatic cancer, bladder cancer, bronchial carcinoma, breast cancer, corpus carcinoma, CUP syndrome, intestinal cancer, small intestines tumors, ovarian cancer, endometrial carcinoma, gall-bladder cancer, uterine cancer, cervico-uterine cancer, glioblastoma, brain tumors, brain lymphomas, metastases of the brain, testicular cancer, hypophyseal tumor, carcinoids, laryngeal cancer, bone cancer, head and neck tumors, colon carcinoma, craniopharyngeomas, liver cancer, metastases of the liver, eyelid tumor, lung cancer, stomach cancer, medulloblastomas, melanoma, meningeomas, mycosis fungoides, neurinoma, kidney cancer, non-Hodgkin lymphomas, oligodendroglioma, oesophageal carcinoma, ovarial carcinoma, pancreatic carcinoma, penis cancer, prostate cancer, throat cancer, rectal carcinoma, retinoblastoma, vaginal cancer, thyroid carcinoma, oesophageal cancer, spinalioma, thymoma, urethral cancer, vulvar cancer, soft-tissue tumors, cervical carcinoma.

Further preferred embodiments and aspects of the inventions can be gathered from the claims, the description and the examples.

DESCRIPTION OF THE INVENTION

In the description, "postembryonic stem cells" stand for somatic stem cells, in particular for stem cells from human umbilical cord blood. Non-expanded stem cells that have been freshly isolated from the umbilical cord blood are termed "initial cells". The phrase "while avoiding differentiation" means that the stem cells are maintained, at least numerically, during the in vitro cultivation. In the ML-IC assay, the stem cell property of the multiplied cells is controlled and confirmed, as described in more detail below. Furthermore, the expanded myeloid and lymphatic progenitor cells generated by proliferation are quantified in the LTC-IC assay (myeloid) and in the LY-IC assay (lymphatic), as is described below.

Therefore, one aspect of the invention is a method for the in vitro generation of immunocompetent cells (NK and NKT cells) by expanding postembryonic stem and progenitor cells from umbilical cord blood. The method is characterized in that the initial cells are cultivated in a medium comprising a regioselectively and stereoselectively modified glycan and/or glycosaminoglycan, while avoiding unwanted differentiation, the modifications being such that this glycan comprises N- and/or O-bonded sulfate, amino, acetyl and/or acyl groups along the polymer chain. Particularly preferably, the $C_2$ atom, in one or more monomer units, is acylated or acetylated, and the $C_6$ atom is O-sulfated. In other words, in the method according to the invention, the umbilical cord blood initial cells, while avoiding differentiation, are multiplied in such a manner, that, on the one hand, the stem cells are at least maintained, and that primitive progenitor cells that are myeloid-determined or lymphatic-determined are generated parallel thereto. It is therefore the aim of the propagation that two stem cells are the result of a cell division, of which at least one with a stem cell function is maintained, while the other one differentiates into a defined progenitor, or, in the case of an asymmetric division, that one stem cell and one progenitor cell are produced, the latter being capable of differentiating into immunocompetent NK and NKT cells.

This effect of stem cell maintenance or stem cell propagation and progenitor cell generation is achieved by means of an in vitro cultivation in a culture medium containing a modified glycan and/or glycosaminoglycan, wherein, in one or more monomer units, the $C_2$ is acylated or acetylated and wherein the $C_6$ atom is O-sulfated. As a rule, heparin molecules consist of unbranched chains of sulfated saccharide components that mainly contain glucosamine, glucuronic acid, and iduronic acid; they have different molecular weights of between 4,000 and 50,000 Dalton. The average weight of the heparins is about 16,000 Dalton. Due to the many carboxyl and sulfate groups, heparin is highly negatively charged and therefore forms complexes with basic proteins under physiological conditions. If the glycan or glycosaminoglycan modified according to the invention is a heparin derivative, 80% or more of the glucosamine units must have a 6-O-sulfate group. A selective 6-O-desulfatation drastically reduces the differentiation arrest during the stem cell expansion. Furthermore, the 2-O-sulfate group of the iduronic acid units is important for the differentiation arrest. The 2-O-sulfate group should be present in 60% or more of the heparin. A 2-O-desulfatation significantly reduces the arresting activity. In contrast, the N-sulfate groups on the glucosamine units must be removed and replaced with N-acetyl or N-acyl groups of different lengths, preferably with 3 to 18 carbon atoms, preferably with 2 to 12, and most preferably with 3 to 6 carbon atoms. The N-desulfatation of the heparin derivative alone does not effect any arresting activity. In addition, 5% or less of the glucosamines in the heparin derivative should carry a 3-O-sulfate group. The molecular weight of the modified heparin derivative is ideally about 10 kDa. Heparin from intestinal porcine or bovine mucosa or kidney can be used as the initial source for the production of modified heparins. Furthermore, partially synthetic heparinoids from polysaccharides of natural origin are also possible, according to the invention/The person skilled In the art knows various other sources for glycans, glycosaminoglycans and sulfated heparinoid polysaccharides that have comparable or equivalent structures after an appropriate modification.

Umbilical cord blood is an advantageous source of somatic stem cells, for there are hardly any or no ethical objections against their use. In addition, the human postembryonic stem and progenitor cells from umbilical cord blood are ontogenetically naive and very immature, which is a great advantage for the desired therapeutic goals. The clinical therapeutic use of these cells was limited to mainly pediatric patients with a body weight of less than 40 kg, due to the small number of cells in most of the available umbilical cord transplants. These stem cells could not be expanded using the known stroma-free in vitro methods, and it was not possible to generate a sufficient quantity of immune effector cell with them. The main problem was the induction of uncontrolled differentiations while at the same time losing stem cells from the initial population used.

The experience gained so far showed that the infantile remnant blood (CB or Cord Blood) remaining in the placenta after exumbilication, which can be extracted through the umbilical cord, as a rule contains enough primitive haematopoietic stem cells (HSC) to achieve a haematological and immunological reconstitution also in adults, and not just in children. Due to the insufficient number of myeloid and lymphatic progenitor cells, and in particular because of the naivity of the immune cells, the use of CB for stem cell transplantation in adults was medically limited because haematological reconstitution times that were too long significantly increased mortality as compared to the bone marrow transplantation. However, it is the advantage of CB that it contains a large population of primitive stem cells with an increased proliferation and stem cell potency. In the recent past, several reports have demonstrated that stem cell transplantations from umbilical cord blood are also advantageous in allogenic transplantations in patients having malignant system diseases: stem cells from umbilical cord blood have decisive advantages over those from bone marrow or from peripheral blood: i) They can be extracted quickly and easily without any physical stress on a donor, ii) There is a significantly lower risk of transmitting viral diseases (in particular of the cytomegalovirus), iii) The risk of a GvHD disease (graft versus host disease) is substantially lower, so that up to 3 HLA mismatches can be accepted with comparable results. There are umbilical cord blood preparations as so-called finished medicinal products which are completely pre-tested and stored and which are available within a very short time. However, the therapeutic use for haematological transplantations was limited not only because of the small number of cells in the transplants, but also because of the long reconstitution phase which was followed by the corresponding clinical complications after the transplantation. These problems are eliminated with the method according to the invention and the immunotherapeutic agents provided therewith.

Though the activity of the immunological effector cells from umbilical cord blood is greatly reduced in comparison with adult sources, this has ah advantage, too, since it contributes to a lower incidence and severity of a GvHD. On the other hand it results in an increased morbidity and mortality due to complications from infections in umbilical cord stem cell transplantations. However, these problems are also solved by the ex vivo generation of immunocompetent cells according to the invention.

It was demonstrated in many studies that particularly the NK cells play an important role in allogenic transplants where the alloreactive donor NK cells do not only kill residual leukaemia cells but also T cells and antigen-presenting cells of the host and participate in the initial defense against infections after the transplantation. These immune reactions are controlled through interactions of so-called "killer immunoglobulin-like receptors" (KIRs) and so-called natural cytotoxicity receptors (NCRs) on the donor NK cell with certain antigens of the major histocompatibility complex class I (MHC CI. I) on the host cells.

For these reasons, an ex vivo expansion with subsequent functional maturation of primitive CB progenitor cells, in particular with a potential to differentiate into NK cells, is important for a successful stem cell transplantation. To this end, few primitive cells must be expanded so that there are enough progenitor cells available in order to then generate a clinically applicable therapeutic agent by further differentiation—inter alia into NK and NKT cells.

In the prior art, different culture additives were hitherto used in the ex vivo expansion of human stem cells from bone marrow and CB—different combinations of cytokines, stroma cell feeder layers, bioreactors. At the moment, the state of the art is contradictory or, in many cases, not reproducible. It is also not clear whether the stem cells maintain their properties and their capability for multilineal differentiation and autoregeneration in the described ex vivo cultures for the expansion of the number of cells and for the induction of proliferation, and whether they are suitable for transplantation. All in vitro culture systems so far simultaneously effect an uncontrolled surge of differentiation during the proliferation of the stem cells. The expansion of the number of cells alone, phenotypical characteristics such as CD34 or the expansion of progenitors in lineage determined assays does not yield information on the stem cells, whether they are still capable of regenerative autoregeneration and multilineal differentiation afterwards.

The difficulty lies in the analysis of the human stem cells in general and particularly in the analysis of the stem cells expanded in vitro as regards cell number, quality and degree of differentiation. There are several in vitro assays established that analyze primitive haematopoietic progenitor cells: the Long Term Culture Initiating Cell (LTC-IC) assay and the "cobblestone area forming cell assay" (CAFC). Combined with the "Limiting Dilution Assay" (LDA), they allow a statement on the occurrence of LTC-IC or CAFC. The problem is, however, that, after an expanded In vitro cultivation, these assays do not permit any statements on the capability for multilineage, that Is, the myeloid, lymphatic, erythrocytic and thrombocytic autoregeneration and for differentiation of the primitive stem cells still present—which is important, however, for the investigation into the effectiveness of the in vitro cultivation. The number and characteristics of human stem cells has so far been examined In very complicated xenogenous animal models (in utero sheep, NOD-SCID mouse). A characterization of the expanded stem cells on the basis of a cell surface marker analysis without functional testing at the same time is not sufficiently reliable. The NOD-SCID mouse model showed that ex vivo expanded human stem cells did carry the surface markers typical for primitive stem cells, but that they were not capable anymore of autoregeneration in the SCID mouse.

There are no reports so far, however, on a directed expansion and generation of stem cells from umbilical cord blood for use as a therapeutic agent. Though it is known that complexes of cationic chitosan and various glycosaminoglycans, in particular of heparin and chondroitin sulfate B, as a solid phase and with the addition of stem cell factor and IL-3, can promote the expansion of $CD34^+$/CB cells. However, the status of differentiation of the $CD34^+$ cells was not examined. In addition, it was known that heparan sulfates that were synthesized from certain stroma cells have an influence on the growth and the differentiation of primitive human haematopoietic bone marrow stem cells (BM-HSC) and that such BM-HSCs, without the addition of stroma cells, can only be maintained up to a maximum of 80% for a period of 5 weeks, in vitro in the presence of certain glycosaminoglycans. Here, only the 6-O sulfatation of the heparin was the essential structural element of the heparin was described, which triggers the effect. The growth-promoting effects could not be achieved with desulfated, N-sulfated or unmodified heparin, which underlines the specific effect of the modifications according to the invention. Though it was known, moreover, that 6-O-sulfated heparins were capable of maintaining up to 80% of exclusively myeloid determined cells (long term culture inducing cells, LTC-IC) from human bone marrow for five weeks. However, an expansion of the primitive stem cell pool was not effected. In addition, it was not examined what the extent of the influence of such heparins and polysaccharides was on primitive and multipotent haematopoietic stem cells with regard to cell growth and differentiation into therapeutically active immune cells. The invention is based upon the surprising discovery that certain regio-specific modifications on glycan and/or glycosaminoglycans, such as on heparin, arrest the differentiation during the ex vivo expansion cultivation of postembryonic stem and progenitor cells from CB, thus enabling a subsequent differentiation into immunocompetent cells.

The method claimed permits the expansion of primitive postembryonic stem cells from a small number of cells while maintaining the stem cells at least numerically, and, in parallel, generating and expanding myeloid and lymphatic progenitor cells. By means of the method according to the invention, the stem cells can be multiplied in vitro so that a (re) implantation of the expanded cells can be applied, also in clinical conditions, both for the regeneration of the haematopoiesis as well as for specific replacement of tissues and organs. The method according to the invention ensures that the stem cell population in the umbilical cord blood is reproducibly stimulated to proliferate by specific use of regio-selectively and/or stereoselectively modified glycans, with the multipotent stem cells being maintained or multiplied, and myeloid or lymphatically determined progenitors being expanded or generated during proliferation.

By the application according to the invention of the glycans or glycosaminoglycans in a so-called "in vitro stem cell culture system", therapeutically applicable progenitor cells from postembryonic tissues can be expanded or generated, which can both be used in umbilical cord blood transplantations and as an independent cellular therapeutic agent in the case of tumor diseases or viral diseases (e.g. hepatitis C or HIV). The following diseases can be taken into consideration: malignant system diseases, acute leukaemias, chronic leukaemias, myeloproliferative syndrome (MPS), myelodysplastic syndrome (MDS), high-grade malignant non-Hodgkin lymphomas (NHL), low-grade malignant NHLs, Hodgkin's disease, multiple myeloma, Waldenström's syndrome, histiocytosis X, amyloidosis and solid tumors such as anal carcinoma, astrocystoma, basalioma, pancreatic cancer, bladder cancer, bronchial carcinoma, breast cancer, corpus carcinoma, CUP syndrome, intestinal cancer, small intestines tumors, ovarian cancer, endometrial carcinoma, gall-bladder cancer, uterine cancer, cervico-uterine cancer, glioblastoma, brain tumors, brain lymphomas, metastases of the brain, testicular cancer, hypophyseal tumor, carcinoids, laryngeal cancer, bone cancer, head and neck tumors, colon carcinoma, craniopharyngeomas, liver cancer, metastases of the liver, eyelid tumor, lung cancer, stomach cancer, medulloblastomas, melanoma, meningeomas, mycosis fungoides, neurinoma, kidney cancer, non-Hodgkin lymphomas, oligodendroglioma, oesophageal carcinoma, ovarial carcinoma, pancreatic carcinoma, penis cancer, prostate cancer, throat cancer, rectal carcinoma, retinoblastoma, vaginal cancer, thyroid carcinoma, oesophageal cancer, spinalioma, thymoma, urethral cancer, vulvar cancer, soft-tissue tumors, cervical carcinoma.

The method according to the invention is based on the application of defined glycans or glycosaminoglycans by means of regio- and/or stereoselective modification (removal, coupling) of functional side groups (e.g., carboxyl, sulfate, acetyl, acyl, amino groups), e.g. on known glycan skeletons ($\alpha$1-4 glycans, $\beta$1-3 glycans, $\beta$1-4 glycans, $\beta$1-3, $\beta$1-4 glycosaminoglycans, $\beta$1-3, $\beta$1-4, $\alpha$1-3 glycosaminoglycans and $\beta$1-4, $\alpha$1-4 glycosaminoglycans). These compounds are defined with regard to (a) the molecular mass, (b) their degree and pattern of sulfatation and (c) the number of other aforementioned functional side groups and distribution of the functional groups in the monomer unit and along the polymer chain.

The changes of the side groups for use according to the invention on the one hand consist of a modification of a side group on the C2 atom of the monomer unit of the glycan or glycosaminoglycan, preferably of the desulfatation and reacylation or reacetylation, so that defined relationships of the side groups on the C2 atom along the polymer chain are created. On the other hand, the presence of a side group having a negative charge, preferably a 6-O-sulfate group, on the C6 atom of the monomer unit of the glycan or glycosaminoglycan is a steric precondition for the method according to the invention. The percentage of the entire modified side groups on the C2 and/or C6 atoms depends on the respective modification, and the most favorable percentage for the method according to the invention can be easily determined by the person skilled in the art by means of the assays mentioned in the following example.

These compounds can be used as additives in expansion and differentiation cultures of postembryonic stem cells for all clinical and industrial applications. One of the essential advantages of the invention is the use of individual substances, which are chemically exactly defined, for the reproducible expansion and generation of postembryonic progenitor cells.

In the experiments that led to the present invention, primitive haematopoietic stem cells were maintained in their original primitive state in vitro while adding polysaccharides according to the invention and defined cytokines, without the co-cultivation of stroma cells or other feeder cells, and at the same time, directed progenitor cells were generated. The potential for differentiation of these cells was demonstrated on a single cell level in subsequent cultures. The used polysaccharides with defined functional groups are characterized by their defined proportion of 6-O-sulfate and N-sulfate groups, 2-O- and 3-O-sulfates groups, as well as N-acetyl or N-acyl groups. They are regioselectively or stereoselectively sulfated and acteylated/acylated repeating units of polysaccharides with defined average degrees of substitution for the individual groups that can be adjusted differently. By the conformation of the respective side groups having different characteristics (hydrophilic, e.g. —$SO_3$; hydrophobic, e.g. -acyl) and the defined distribution along the polymer chain, the hydrophobic and hydrophilic relationships within the glycan or the glycosaminoglycan are changed substantially.

Thus, the present invention relates to a method for the selective propagation of postembryonic stem cells while avoiding differentiation, characterized by the initial cells being cultivated in a medium comprising a modified glycan and/or glycosaminoglycan, the modification being such that the original side group of the C2 atom of one or more monomer units of the glycan and/or glycosaminoglycan is modified and the side group of the C6 atom of one or more monomer units of the glycan and/or glycosaminoglycan is a side group with a negative charge, preferably a 6-O-sulfate group.

The glycan and/glycosaminoglycan is preferably an α1-4 glycan, β1-3 glycan, β1-4 glycan, β1-3, β1-4 glycosaminoglycan, β1-3, β1-4, α1-3 glycosaminoglycan and/or β1-4, α1-4 glycosaminoglycan. Preferably, the C2 atom of one or more monomer units is desulfated and a new side group is introduced on the C2 atom, preferably a acetyl, acyl(preferably butyl), amino or carboxymethyl group. Particularly preferred is an acetyl or acyl group. Reacetylation is understood to be the coupling of a acetyl group to the C2 atom of the monomer unit.

The most advantageous percentage of the respective modified C2 and/or C6 atoms can be determined by means of the functional assays described below.

The carbohydrate basic structures used in the present application are compounds as defined by the "IUPAC-IUB Joint Commission on Biochemical Nomenclature (JCBN)" (Eur. J. Biochemistry 126 (1982), 439-441), and as described by S. Dumitriu (Polysaccharides in Medical Applications. Marcel Dekker, 1996) as well as by J. Lehmann (Kohlenhydrate, Chemie und Biologie, G. Thieme Verlag, 1996). Here, all oligo and polysaccharides that may, in their sequential structure, be both homoglycans consisting of one monosaccharide repeating unit, as well as heteroglycans consisting of various monosaccharide repeating units, are subsumed under the term glycans.

Compounds in which monosaccharides are linked together by glycosidic bonds are subsumed as oligosaccharides/polysaccharides. Here, oligosaccharides and polysaccharides having repetitive saccharide sequences are subsumed as glycans. The term "oligosaccharide" denotes glycans consisting of 2 to 10 monosaccharide units, whereas the term "polysaccharide" comprises all glycans consisting of more than 10 monosaccharide units.

Heteroglycans having repetitive disaccharide units that respectively consist of an amino sugar and an uronic acid, which differ from one another with regard to their monosaccharide units and their glycosidic bond, are defined as glycosaminoglycans.

The glycans or glycosaminoglycans that can be used in the method according to the invention can have different degrees of linking and branching, i.e., they can be, e.g., linear, branched or cyclic (e.g. β-cyclodextrin). With regard to their molecular weight, the glycans or glycosaminoglycans that can be used in the method according to the invention are not subject to any limitation, however, the biological activity is obviously better in larger molecules. Favorable molecular weights are in the range from about 10 to 35 kD or above.

By means of generally known methods, e.g. by means of classic protective group techniques and/or solid phase synthesis, the person skilled in the art is able to produce the poly/oligosaccharides suitable for the method according to the invention. Methods for removing or coupling side chains, e.g. for the regioselectrve and stereoselective modification, are also generally known; see for example Baumann et. al., Carbohydrate Res. 308 (1998), 391-388; 331 (2001), 43-57; Baumann et. al., Carbohydrate Res. 337 (2002), 1297-1307, Baumann et. al., Macromol. Chem. Phys. 201 (2000), 1950-1962; German patent 4444445.1; Huppertz et. al., In: Frontiers in Biomedical Polymer Applications (Eds. Ottenbrite, Chiellini, Cohn, MigliaFresi, Sunamoto), Vol. 2, pp. 115-129, Technomic 1999; Grootenhuis et. al., Nat. Struct. Biol. 2 (1995), 736-739; Westerduin et. al., Bioorg. Med. Chem. 2 (1994), 1267-1280; Wessel et. al., Carbohydr. Res. 204. (1990), 131-139; Matsuo et. al., Carbohydr. Res. 241 (1993), 209-215; Kurita et. al., Macromolecules 31 (1998), 4764-4769; Kariya et. al., J. Biol. Chem. 275 (2000), 25949-25958; Du et. al., Carbohydr. Res. 329 (2000), 17-24; and Groth and Wagenknecht, Biomaterials 22(2001), 2719-2729.

The person skilled in the art also knows suitable cultivation methods and media for cultivating postembryonic stem cells, see e.g. DE 196 08 813 C2 or EP-B1 0 695 351 or the following example. The person skilled in the art is also able to determine the optimal concentration of the modified glycan or glycosaminoglycan for the desired purpose by means of simple experiments. The "basic medium", which inter alia contains a glycan or glycosaminoglycan modified according to the invention, can be any medium usually used for expanding stem cells. In a preferred embodiment of the medium according to the invention, the "basic medium" in which, inter alia, a glycan or glycosaminoglycan according to the invention is contained, is IMDM ("Iscove's Modified Dulbecco's Medium"; Invitrogen). The desired stem cells are cultivated in the above-mentioned medium under suitable conditions, if necessary, (partially) renewing the medium at suitable intervals. Suitable conditions, for example with regard to suitable containers, temperature, relative humidity, $O_2$ content and $CO_2$ content of the gas phase, are known to the person skilled in the art. Preferably, the cells are cultivated in the above medium under the following conditions: (a) 37° C., (b) 100% RH, (c) 10% $O_2$ and (d) 5% to 7% $CO_2$. The person skilled in the art can also monitor the desired control of the differentiation of the animal cells by usual criteria (morphological criteria, presence or absence of specific surface proteins, etc.; in this regard, see the assays in the example below).

A further preferred embodiment of the method according to the invention relates to the isolation and/or enrichment and/or selective propagation of postembryonic stem cells using a medium containing 2-O-desulfated heparin, N-desulfated and/or N-desulfated and reacetylated heparin. The cultivation or maintenance of the cells takes place as described above or in the example below.

The person skilled in the art can determine the concentrations of the modified glycans or glycosaminoglycans suitable for the expansion method according to the invention by means of simple experiments. In a preferred embodiment of the expansion method according to the invention, the modified glycan or glycosaminoglycan is present in the culture medium in a concentration of 2 to 50 mg/l, a concentration of 10 mg/ml being the most preferred.

The following non-embryonic human stem cells can be used for the cultivation method according to the invention: somatic stem or progenitor cells, haematopoietic stem cells being preferred. The person skilled in the art knows sources for the extraction and expansion of those stem cells. Haematopoietic stem cells can for example be obtained from fetal liver, umbilical cord blood or bone marrow, the extraction from umbilical cord blood being preferred for the method according to the invention.

In a further preferred embodiment of the method according to the invention, a functional detection of the properties of the stem and progenitor cells follows the cultivation. The examples below illustrate the invention.

EXAMPLE 1

Expansion Cultivation of Haematopoietic Progenitor Cells by Means of Modified Heparins as Additive to the Cultivation Medium Stem-cell-enriched umbilical cord blood cells were cultivated for five weeks in a defined and clinically applicable expansion system, with the addition of glycans according to the Invention, and the expansion of primitive myeloid and lymphatic progenitor cells as a sign of the propagation of the stem cells (quantifiable as ML-IC; "Myeloid-Lymphoid-Initiating Cells") was determined.

The culture medium consisted of "Iscove's Modified Dulbecco's Medium" (Invitrogen, Karlsruhe) with 12.5% fetal calf serum and 12.5% horse serum (Stem Cell Technologies, Vancouver, Canada). The sterilized glycans described in table 1, which have functional side groups, are supplemented in a concentration of 20 mg/l, and the following additives are supplemented as well: 2 mmol/l L-Glutamin (invitrogen), Penicillin (1000 U/ml), Streptomycin 100 U/ml (Invitrogen), $10^{-6}$ mmol/l hydrocortisone, 25 µM 2-mercaptoethanol-B, 10 pg/ml GM-CSF (Immunex Corp., Seattle, Wash.), 250 pg/ml G-CSF (Amgen, Thousand Oaks, Calif.), 200 pg/ml SCF (Stem Cell Technologies), 50 pg/ml LIF (Stem Cell Technologies), 200 pg/ml MIP-1 alpha (Stem Cell Technologies), und 50 pg/ml IL-6 (Stem Cell Technologies), 10 ng/ml Flt-3L and 10 ng/ml thrombopoietin (Immunex Corp., Seattle, Wash.).

The cultures were maintained at 37° C. and 5% $CO_2$ with a change of medium every 48 hours for 5 weeks, then, the expansion of the stem cell equivalent multipotent cells was determined in the ML-IC assay (detection of LTC-IC and NK-IC).

ML-IC assay: The ML-IC assay (Punzel et. al., Blood 93 (1999), 3750-3756) was used for testing the properties of the stem cells of the umbilical cord blood Cells cultivated ex vivo. The cells of the primary cultures were brought uniformly into suspension by mechanical pipetting, and then, the content of each individual primary culture (200 µl) was brought into 4 new, already pre-established AFT024 stroma-dependent secondary cultures (50 µl primary suspension per secondary culture), in such a way that each of the 4 secondary cultures of a primary single cell was in the same position on the new microtitre plates. This ensured that all secondary progenitors could be allocated to the primary single cell. Two of the secondary cultures were cultivated for five weeks under myeloid conditions in the secondary LTC-IC assay. The other two cultures were also cultivated for another 5-7 weeks in the LY-IC assay under lymphatic in vitro differentiation conditions, and then examined for mature functional NK cells as described below.

LTC-IC assay (Gupta et al. Blood 95 (2000). 147-155): Freshly sorted single cells (day 0) or the entire progeny of a single cell (day 14) were cultivated in AFT024 cultures with long term culture (LTBMC) medium (IMDM/12.5% FCS/12.5% horse serum as well as penicillin/streptomycin and $10^{-6}$ mmol hydrocortisone) (one change of medium every seven days). The medium was removed after 5 weeks and the culture was provided with semi-solid methyl cellulose medium (1.12% methyl cellulose, IMDM/30% FCS, 3 IU/ml erythropoetin, 7.5% cytokin-containing supernatant of the cell line 5637 ATCC HB-5). Single cells with the capability for generating secondary colony-forming cells (CFC) were called LTC-IC according to the definition.

LY-IC assay: Freshly sorted single cells (day 0) or the entire progeny of a single cell (day 14) were cultivated in AFT024 cultures in a lymphatic differentiation medium (DMEM/Ham's F 12 medium 2:1 (V/V) with 20% human heat-inactivated AB serum as well as 20 mg/ml ascorbic acid, 50 µmol selenium, 25 µmol mercaptoethanol, 50 µmol ethanolamine. 1000 U/ml IL-2, 5 ng/ml IL-3 [only on day 0], 10 ng/ml Flt-3L, 10 ng/ml SCF and 20 ng/ml IL). After 5-7 weeks, all cultures with a visually objectivizable clonal cell proliferation were harvested by mechanical pipetting, and examined for mature NK cells (CD56+/CD3−), NKT cells (CD3+/CD56+) and also for Pro-B cells (CD19+/CD56−) by means of FACS analysis.

Primary cultivated cells that were capable of generating both LTC-IC as well as lymphatic effector cells, are then stem cell equivalent ML-IC. The expansion of the umbilical cord blood cells is calculated from the ratio of immature LTC-IC and NK-IC before and after the expansion culture. The results of the above tests are shown in table 1.

TABLE 1

| Expansion | H0 | H0-1 | H1 | H2 | H3 | H3-1 | C1 | C2 |
|---|---|---|---|---|---|---|---|---|
| Myeloid | 1.0 | 0.9 | 3.9 | 10.7 | 11.8 | 4.1 | 0.3 | 2.0 |
| Lymphatic | 1.0 | 1.1 | 15.2 | 11.7 | 12.4 | 5.0 | 7.4 | 7.7 |

H0: standard unmodified heparin with low 3-O-sulfate content;
H0-1: standard unmodified heparin with increased 3-O-sulfate content (initial heparins for regioselective modifications);
H1: 2-O-desulfated standard heparin, from H0
H2: N-desulfated standard heparin from heparin H0;
H3: N-desulfated and reacetylated standard heparin from heparin H0;
H3-1: N-desulfated and reacetylated standard heparin from heparin H0-1;
C1: chitosan N-sulfated;
C2: chitosan N-desulfated and N-acetylated.

In the heparins, 2-O-sulfate is the sulfate group on C2 of the iduronic acid unit, 3-O-sulfate is the sulfate group on C3 of the glucosamine unit, 6-O-sulfate is the sulfate group on C6 of the glucosamine unit, 2-N-sulfate and N-acetate are the N-sulfate and N-acetyl group on C2 of the glucosamine unit, respectively. The average molecular weight of the heparins used was 10-12 kDa.

As starting material for chitosan, crab-derived by FLUKA with a molecular weight of approximately 150 kDa and cleaved into fragments of 29 kDa by hydrolysis. No expansion of the stem cell cultures was achieved with this hydrolyzed initial chitosan (results not shown).

The actual stem cell expansion is the result of the combined increase of the myeloid and lymphatic expansion capability in the CB-HSC manipulated in the above expansion conditions. The addition of regioselectively and stereoselectively modified glycans, in comparison with the cultures with unmodified heparin (H0 and H0-1), shows a significant expansion effect. These results make it clear that a desulfatation on the C2 atom with reacetylation or acylation is responsible for the effect on the expansion of CB-HSC brought about by modified glycans.

TABLE 2

| Regioselectively modified glycan | 2-O-sulfate | 3-O-sulfate | 6-O-sulfate | 2-N-sulfate | 2-N-acetyl | 2-N—$CH_2$—COOH |
|---|---|---|---|---|---|---|
| H0 | 60% | 5% | 90% | 90% | 7% | — |
| H0-1 | 58% | 33% | 90% | 88% | 5% | — |
| H1 | 9% | 6% | 85% | 90% | 5% | — |
| H2 | 60% | 0% | 85% | 0% | 14% | — |
| H3 | 60% | 5% | 85% | 0% | 100% | — |

TABLE 2-continued

| Regioselectively modified glycan | 2-O-sulfate | 3-O-sulfate | 6-O-sulfate | 2-N-sulfate | 2-N-acetyl | 2-N—CH$_2$—COOH |
|---|---|---|---|---|---|---|
| H3-1 | 58% | 33% | 83% | 0% | 100% | — |
| C1 | — | 0% | 70% | 88% | 12% | 38% |
| C2 | — | 0% | 0% | 59% | 41%* | 0% |

It can be seen from table II that, according to the invention, in the total polymer, more than 80% require a 6-O-sulfate group at the glucosamine monomer unit in heparins. A selective O-6-desulfatation according to H. Baumann et. al., Carbohydrate Res (1998) 308, 381-388, results in a drastic reduction of the functional activity in the stem cell expansion. The 2-O-sulfate group of the iduronic acid monomer unit also contributes to the activity and should be present in a proportion of >60% of the total polymer. O-2-desulfatation also reduces the activity significantly. The N-sulfate group of the glucosamine monomer unit must be totally eliminated and be replaced with an N-acetyl or N-acyl group of different length. The N-desulfatation alone does not result in an increased activity. The 3-O-sulfate group of the glucosamine monomer unit should be less or equal to 5% of the total polymer. The molecular weight of the modified heparin derivative should ideally be about 10 kDa. Heparin from intestinal porcine or bovine mucosa or kidney can be used as the source for the production of modified heparins. Sodium heparinate from porcine mucosa of highest purity, suitable for research purposes, activity 178,000 IU/g (SERVA, Heidelberg, Germany) was used as starting material for the experiments. The other chemicals were, if not stated differently, pure substances by the companies Aldrich, Fluka or Sigma.

An example for a functionally active modified heparin is a N-desulfated, N-reacetylated heparin having the following structure.

Modified Heparin with Altered Sulfatation and Acetylation

| Heparin | 2-O—S | 3-O—S | 6-O—S | C2-N—S | N—Ac | O—Ac | NH2 |
|---|---|---|---|---|---|---|---|
| | 63% | 5% | 84% | 0% | 100% | 0% | 0% |

The characterization of the heparin derivatives was carried out by means of 13C NMR spectroscopy at 75 MHz. The signals were identified according to B. Casu et. al., Arzneimittelforschung 33, 135-142, 1983; E. A. Yates et. al., Carbohydrate Res. 294, 15-27, 1996. The quantification of the various sulfate groups was carried out according to Casu et. al., Arzneimittelforschung 33.135-142, 1983. The molecular weights were determined by means of column chromatography. The columns were calibrated with kerato sulfates of defined molecular weights [H. Butz et. al. J. Biol. Chem. 267, 34023408.1992]. Regioselective modification on C3 and C6 of the glucosamine monomer unit, N-acetylation and N-carboxymethylation on C2 of the monomer glucosamine unit were carried out according to Baumann H and Faust V, Regioselektive Modifikationen der Chitosane, Carbohydrate Res. (2001) 331, 43-57.

EXAMPLE 2

Production of an Immunotherapeutic Agent

For the application conforming to GMP (good manufacturing practice), pre-expanded cells were further expanded in a suspension culture under the following conditions:

DMEM/Ham's 12 medium 2:1 (V/V) with 10% human heat-inactivated AB serum as well as 20 mg/ml ascorbic acid, 50 µmol selenium, 25 µmol mercaptoethanol, 50 µmol ethanolamine, 1000 U/ml IL-2, 10 ng/ml Flt-3L, 10 ng/ml SCF, 20 ng/ml IL-7, 10 ng/ml IL-15 and 10 ng/ml IL-21) cultivated. After 3 to 4 weeks, the cells were harvested by mechanical pipetting, and examined for mature functional NK cells by means of FACS analysis, as described below:

a) by flow-cytometry analysis of the surface antigens present. Here, the CD56 (N-CAM) and CD16 (FcRyIII) positive, CD3-negative cells were defined as NK cells through multicolor analysis, and they were then analyzed with regard to their KIR and activator receptors. These cells were positive for specific KIR receptors CD158 (CD158a(KIR2DL1), b(KIR2DL3)) or CD94/CD159a (NKLG2a), as well as for certain Nkp activator receptors, so that a cell-lytic NK cell activity was ensured through the bond to the corresponding MHC Class I antigens on the native cell as molecular precondition for cell lysis.

b) In addition, the lytic activity of the generated NK cells was demonstrated directly through a standard $^{51}$Cr-release assay on K562 cells as target cell. The multipotent stem cells generated by the addition of different polysaccharides showed no differences in quality during the differentiation cultivation with regard to the expression of the above-mentioned surface antigens, the difference could only be seen in the number of expanded cells.

Alternatively, the expanded progenitors can also be brought to maturation in vivo, by additional subcutaneous administration of IL-2 In the patient (Miller et. al., 2005).

Thus, a cellular therapeutic agent is available that can be transfused through a vein into a patient as a blood product. The expanded natural killer cells mentioned, or their progenitors, which then bring about therapeutic effects in the patient, are contained in the cellular product. These so-called natural killer cell therapeutic agents (NKCTA) can be applied both within the context of a stem cell or bone marrow transplantation, as well as used as independent therapeutic agents for the treatment of malignant diseases of the haematopoietic and lymphatic systems and of all other malignant disease. A further advantage is the penetration of the blood-brain-barrier which also makes their use in all cases of malignant brain tumors possible.

Moreover, it is also possible to use them in the treatment of chronic viral diseases (e.g. hepatitis C and HIV).

EXAMPLE 3

Production and Characterization of Modified Heparins

Extraction of heparins with a low 3-O-sulfate content by means of AT III affinity chromatography.

Antithrombin III (AT III) binds to a specific heparin sequence whose basic structure is defined as a pentasaccharide with a 3-O-sulfo group on an inner glucosamine, the sulfo group being an absolute requirement for binding AT III (R. Linhard and I. Capila, Angew. Chemie 2002, 114, 426-

450). Because heparins modified according to the invention must have a very small proportion of 3-O-sulfo groups on the glucosamine monomer unit, an AT III affinity chromatography was applied to a Sepharose CL4B column in order to obtain, in the flowthrough, non-AT III-binding heparins for their further chemical modification. The AT III used for this purpose was isolated from human blood plasma.

The separation of the AT III-binding from the non-AT III-binding heparins was monitored by biomagnetic separation. Magnetic AT III beads were produced for this purpose, in order to separate in a magnetic column the AT III binding fraction of heparins from those that do not bind AT III. AT III was biotinylated using Biotin-X-NHS (Calbiochem). Magnetic beads moistened with strepavidin (Dynabeads M-270 Strepavidin; Dynal) were used in a ratio of 1 ml beads to 200 μg of the AT III biotin. After a 30-minute incubation on the shaker, the magnetobeads were washed again with PBS in the magnetic column in order to remove the unbound AT III biotin. Now, the AT III magnetobeads thus obtained could be used for the AT III binding assay.

AT III Binding Assay:

1 ml of the AT III magnetobeads, respectively, was incubated at room temperature on the shaker for 30 minutes with 1 ml of the heparan sulfate to be examined. The mixture was put into a magnetic support, the supernatant containing the unbound part of the heparan sulfate was lifted off, and the concentration of the heparan sulfate was determined photometrically at 232 nm, calibration curves having been prepared for each heparin before for this purpose. The remaining part that was bound to the AT III magnetobeads was now incubated for 10 minutes with 2M NaCl on a shaker, and the AT III binding was thus broken. Then, the supernatant was removed again in the magnetic support with the heparan sulfate that had binded to the AT III in the first step. Its concentration was then determined photometrically at 232 nm by means of the calibration curve.

The heparin low in 3-O-sulfate thus obtained were then modified partially or totally according to established methods, see Nagasawa K et. al., Glucosamin N-desulfation, Carbohydrate Res. (1977) 58, 47-55; Danishefsky, I et. al., Glucosamin N-reacetylation, Arch Biochem Biophys (1960) 90, 114-121; M. Höök et. al., Glucosamin N-desulfation, Anal Biochem. (1982) 119, 236-245, and as described above in example 2.

The invention claimed is:

1. A method for expanding postembryonic hematopoietic stem cells from umbilical cord blood while, avoiding unwanted differentiation, wherein said postembryonic hematopoietic stem cells can differentiate into myeloid and lymphatic cells, said method comprising providing initial postembryonic hematopoietic stem and progenitor cells from umbilical cord blood and cultivating ex vivo said initial cells in a stroma-free medium and in the presence of a regio-modified glycan and/or glycosaminoglycan, which is modified as follows:
the side group of the C2 atom of one or more monomer units of the glycan and/or glycosaminoglycan has an acetyl or acyl group with 2 to 12 carbon atoms; the side group of the C6 atom of one or more monomer units of the glycan and/or glycosaminoglycan is a 6-O-sulfate group,
wherein said cultivating generates postembryonic hematopoietic stem cells and progenitor cells that can differentiate specifically into myeloid and lymphatic cells.

2. The method according to claim 1, wherein the region-modified glycan or glycosaminoglycan is selected from α1-4 glycans, β1-3 glycans, β1-4 glycans, β1-3, β1-4 glycosaminoglycans, β1-4, α1-4 glycosaminoglycans, β1-4, β1-3, (α1-3) glycosaminoglycans and β1-4, β1-3, (α1-4) glycosaminoglycans.

3. The method according to claim 1, wherein the region-modified glycosaminoglycan is a heparin derivative that was substantially N-desulfated and N-reacetylated or N-reacylated on the C2 atom, that has C6-O-sulfate groups, and that contains 5 percent or less C3-O-sulfate.

4. The method according to claim 3, wherein the regio-modified glycosaminoglycan is a heparin containing at least 60% C2-O-sulfate and at least 80%, C6-O-sulfate.

5. The method according to claim 1, wherein the region-modified glycan or glycosaminoglycan is present with a concentration of 15 to 50 mg/L in the medium.

6. The method according to claim 1, wherein the properties of the stem cells are monitored in an ML-IC assay.

7. The method according to claim 1, wherein the properties of the generated progenitor cells are monitored in an LY-IC assay (lymphatic) or in a LTC-IC assay (myeloid-erythroid) or in both assays.

8. The method according to claim 1, wherein the stem and progenitor cells propagated under conditions conforming to GMP (good manufacturing practice) are differentiated into functional lymphocytes (NK cells and NKT cells).

9. A culture medium for expanding postembryonic stem and progenitor cells, said culture comprising a growth medium, nutrients, and a region-modified glycan and/or glycosaminoglycan, wherein the side group of the C2 atom of one or more monomer units of the glycan and/or glycosaminoglycan is acylated or acetylated, and wherein the side group of the C6 atom of one or more monomer units of the glycan and/or glycosaminoglycan is a 6-O-sulfate group.

10. A method for expanding postembryonic stem and progenitor cells, said method comprising administering to said cells in a growth medium a region-modified glycan and/or glycosaminoglycan, wherein the side group of the C2 atom of one or more monomer units of the glycan and/or glycosaminoglycan is acylated or acetylated, and wherein the side group of the C6 atom of one or more monomer units of the glycan and/or glycosaminoglycan has a 6-O-sulfate group.

11. A method for the production of a therapeutic agent for the direct administration of expanded stem and progenitor cells, said method comprising the method of claim 1, wherein the therapeutic agent comprises a pharmaceutically acceptable carrier or excipient.

12. The method according to claim 11 for producing a therapeutic agent for the treatment of tumorous diseases, viral diseases, hepatitis C, HIV, malignant system diseases, acute leukaemias, chronic leukaemias, myeloproliferative syndrome (MPS), myelodysplastic syndrome (MDS), high-grade malignant non-Hodgkin lymphomas (NHL), low-grade malignant NHLs, Hodgkin's disease, multiple myeloma, Waldenström's syndrome, histiocytosis X, amyloidosis and solid tumors such as anal carcinoma, astrocystoma, basalimoa, pancreatic cancer, bladder cancer, bronchial carcinoma, breast cancer, corpus carcinoma, CUP syndrome, intestinal cancer, small intestines tumors, ovarian cancer, endometrial carcinoma, gall-bladder cancer, uterine cancer, cervico-uterine cancer, glioblastoma, brain tumors, brain lymphomas, metastases of the brain, testicular cancer, hypophyseal tumor, carcinoids, laryngeal cancer, bone cancer, head and neck tumors, colon carcinoma, craniopharyngeomas, liver cancer, metastases of the liver, eyelid tumor, lung cancer, stomach cancer, medulloblastomas, melanoma, meningeomas, mycosis fungoides, neurinoma, kidney cancer, non-Hodgkin lymphomas, oligodendroglioma, oesophageal, carcinoma, ovarial carcinoma, pancreatic carcinoma, penis cancer, prostate cancer, throat cancer, rectal carcinoma, retinoblastoma, vaginal cancer, thyroid carcinoma, oesophageal cancer, spinalioma, thymoma, urethral cancer, vulvar cancer, soft-tissue tumors, cervical carcinoma.

* * * * *